United States Patent
Ogata et al.

(10) Patent No.: US 12,203,913 B2
(45) Date of Patent: Jan. 21, 2025

(54) ODOR DETECTION SYSTEM, ODOR DETECTION METHOD, AND PROGRAM

(71) Applicant: I-PEX Inc., Kyoto (JP)

(72) Inventors: Kenji Ogata, Ogori (JP); Shunsuke Wada, Ogori (JP); Shohei Takeda, Ogori (JP); Shohei Ushio, Ogori (JP)

(73) Assignee: I-PEX Inc., Kyoto (JP)

(*) Notice: Subject to any disclaimer, the term of this patent is extended or adjusted under 35 U.S.C. 154(b) by 287 days.

(21) Appl. No.: 17/915,076

(22) PCT Filed: Mar. 4, 2021

(86) PCT No.: PCT/JP2021/008470
§ 371 (c)(1),
(2) Date: Sep. 27, 2022

(87) PCT Pub. No.: WO2021/199893
PCT Pub. Date: Oct. 7, 2021

(65) Prior Publication Data
US 2023/0152290 A1    May 18, 2023

(30) Foreign Application Priority Data
Apr. 2, 2020 (JP) .................. 2020-067098

(51) Int. Cl.
*G01N 33/00*   (2006.01)
*G01N 29/32*   (2006.01)

(52) U.S. Cl.
CPC ....... *G01N 33/0062* (2013.01); *G01N 29/326* (2013.01); *G01N 33/0006* (2013.01); *G01N 33/0027* (2013.01)

(58) Field of Classification Search
CPC ............. G01N 33/0062; G01N 29/326; G01N 33/0006; G01N 33/0027; G01N 33/0031
See application file for complete search history.

(56) References Cited

U.S. PATENT DOCUMENTS

| 4,770,027 A | 9/1988 | Ehara et al. |
| 6,575,013 B2 | 6/2003 | Bao et al. |
| (Continued) | | |

FOREIGN PATENT DOCUMENTS

| CN | 1319183 A | 10/2001 |
| CN | 109975488 A | 7/2019 |
| (Continued) | | |

OTHER PUBLICATIONS

Supplementary Partial European Search Report, Application No. EP 21 78 2315, date of completion Jul. 13, 2023, 12 pages, European Patent Office.

(Continued)

*Primary Examiner* — Francis C Gray
(74) *Attorney, Agent, or Firm* — Howard & Howard Attorneys PLLC

(57) ABSTRACT

A substance sensor includes sensitive membranes to react with substances included in the odors of a gas in correspondence with the substances, and is configured to detect the reaction values of the sensitive membranes. An odor specifier specifies the odors of the gas on the basis of the reaction values of the sensitive membranes. A reaction value calculator calculates reaction values corresponding to the odors specified by the odor specifier on the basis of the reaction values of the sensitive membranes. A percentage calculator calculates the percentages of the reaction values corresponding to the odors specified by the odor specifier to the total of the reaction values corresponding to the odors. A display displays the percentages of the reaction values corresponding to the odors, calculated by the percentage calculator, so that comparison of the percentages is enabled between the odors specified by the odor specifier.

15 Claims, 18 Drawing Sheets

(56) References Cited

U.S. PATENT DOCUMENTS

| | | |
|---|---|---|
| 2001/0011473 A1 | 8/2001 | Marshall et al. |
| 2003/0172717 A1* | 9/2003 | Kita .................. G01N 33/0031 73/23.34 |
| 2005/0044928 A1* | 3/2005 | Kita .................. G01N 33/0034 73/23.34 |
| 2005/0208673 A1 | 9/2005 | Labreche et al. |
| 2005/0252275 A1 | 11/2005 | Kita et al. |
| 2018/0088088 A1 | 3/2018 | Shimomai et al. |
| 2018/0238822 A1 | 8/2018 | Chen et al. |
| 2020/0240978 A1 | 7/2020 | Kuroda |

FOREIGN PATENT DOCUMENTS

| | | | | |
|---|---|---|---|---|
| EP | 3 540 420 A1 | 9/2019 | | |
| JP | 2003-315298 A | 11/2003 | | |
| JP | 3501109 B2 * | 3/2004 | ......... | G01N 33/0031 |
| JP | 2004508570 A * | 3/2004 | ......... | G01N 33/0001 |
| JP | 2005-241642 A | 9/2005 | | |
| JP | 2005-291715 A | 10/2005 | | |
| JP | 2006-317254 A | 11/2006 | | |
| JP | 3963306 B2 * | 8/2007 | | |
| JP | 2007-309752 A | 11/2007 | | |
| JP | 2009-204584 A | 9/2009 | | |
| JP | 4374723 B2 * | 12/2009 | | |
| JP | 2018-048930 A | 3/2018 | | |
| JP | 2020-161071 A | 10/2020 | | |
| JP | 2020-161072 A | 10/2020 | | |
| TW | 201912794 A | 4/2019 | | |
| WO | 02/23134 A1 | 3/2022 | | |

OTHER PUBLICATIONS

Supplementary European Search Report, Application No. EP 21 78 2315, dated Oct. 10, 2023, 15 pages, European Patent Office.

Krylov, V. V:, "Odor Space Navigation Using Multisensory E-Nose", Automation and Remote Control, Feb. 2, 2018, vol. 79, No. 1, pp. 167-179.

Fraser, Sheila M. et al., "Development of a Multi-sensor System Using Coated Piezoelectric Crystal Detectors", Analyst, Oct. 1986, vol. 111, No. 10, p. 1183.

Taiwan Office Action dated Jul. 30, 20244, issued for the corresponding Taiwan Patent Application No. 110109531.

* cited by examiner

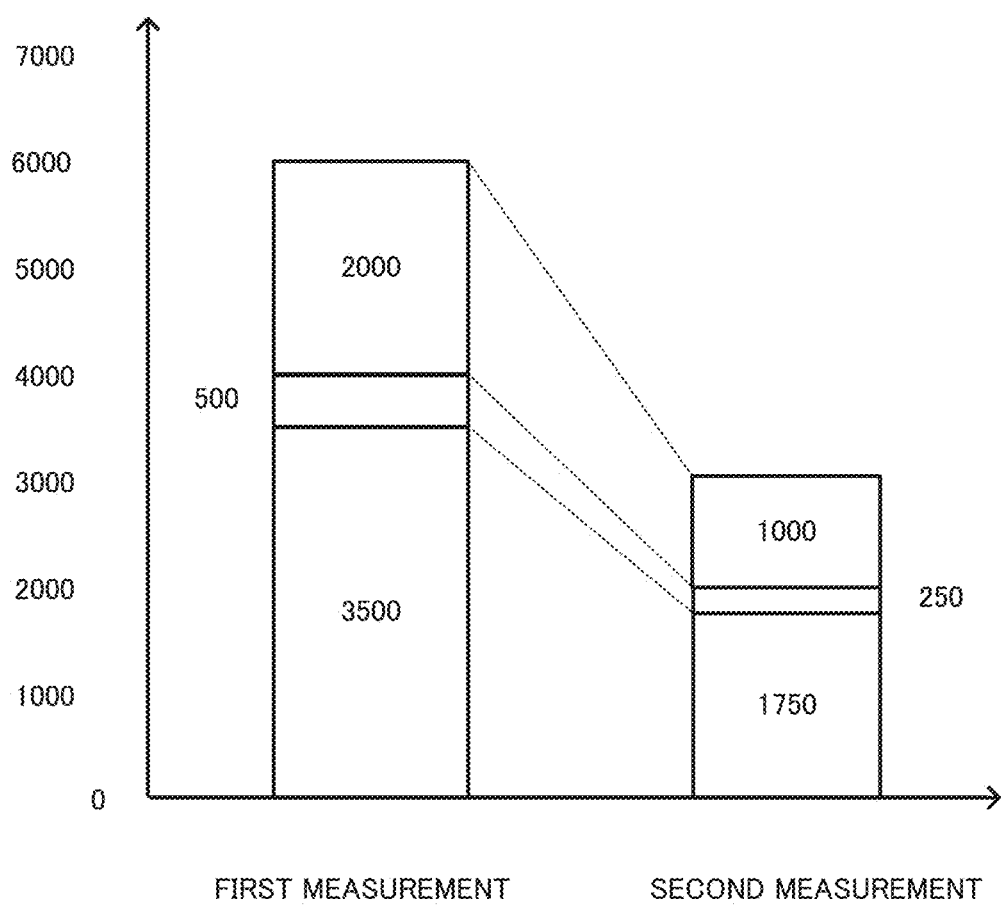

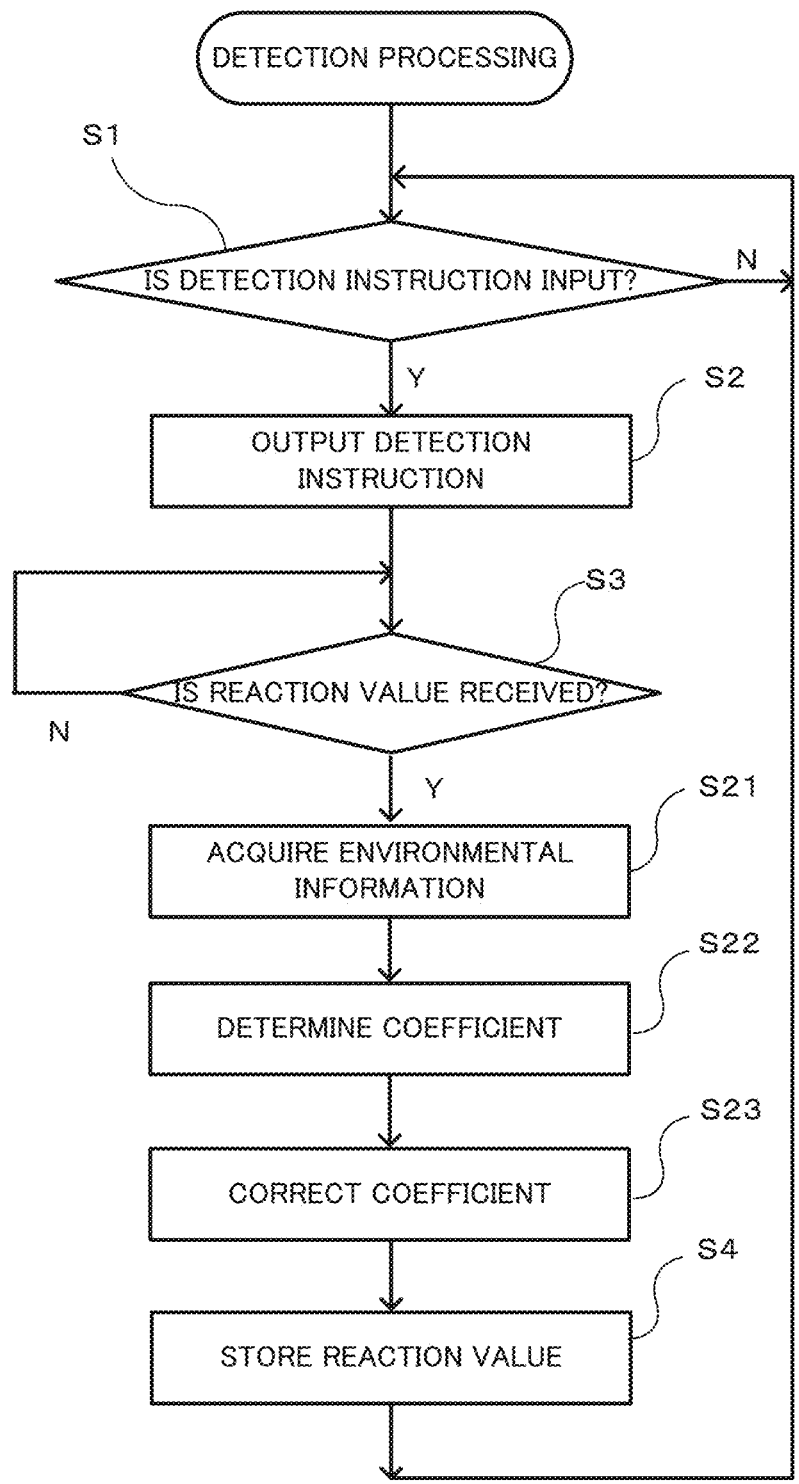

ODOR DETECTION SYSTEM, ODOR DETECTION METHOD, AND PROGRAM

CROSS-REFERENCE TO RELATED APPLICATIONS

This application is a U.S. National Phase application of International Patent Application No. PCT/JP2021/008470, filed Mar. 4, 2021, which claims the benefit of JP Patent Application No. 2020-067098, filed Apr. 2, 2020, the disclosures of which are hereby incorporated by reference in their entirety.

TECHNICAL FIELD

The present disclosure relates to an odor detection system, an odor detection method, and a program.

BACKGROUND ART

Patent Literature 1 discloses a chemical sensor device to detect a substance on the basis of a variation in resonance frequency, occurring when any of sensitive membranes adsorbs or desorbs the substance. The chemical sensor device includes a plurality of vibrators provided with the sensitive membranes exhibiting desorption and adsorption properties for different substances, respectively. Each vibrator, including a piezoelectric substrate, is vibrated by applying an alternating voltage to the piezoelectric substrate to deform the piezoelectric substrate. Adsorption or desorption of a substance on or from any of the sensitive membranes results in variation in the resonance frequency of each vibrator. As a result, detection of the substance is enabled.

In accordance with the chemical sensor device, an odor including a plurality of substances can be detected. The odor of a gas is specified based on the pattern of the reaction values of each sensitive membrane, that is, the composition ratio between the plurality of substances included in the odor.

CITATION LIST

Patent Literature

Patent Literature 1: Unexamined Japanese Patent Application Publication No. 2009-204584

SUMMARY OF INVENTION

Technical Problem

However, the chemical sensor device described above has had a problem that variations in the results of detection of the odor of even a gas in which the composition ratio between substances is identical occurs depending on a difference in situation in detection. This is because the sensitivities of the sensitive membranes are changed depending on an environmental condition such as, for example, a humidity or the number of measurements.

The present disclosure was made under such actual circumstances with an objective to provide an odor detection system, an odor detection method, and a program, in which variations in the results of detection of an odor can be reduced.

Solution to Problem

In order to achieve the objective described above, an odor detection system according to a first aspect of the present disclosure includes:

a substance sensor including a sensitive membrane to react with a substance included in an odor of a gas in correspondence with the substance, the substance sensor being configured to detect a reaction value of the sensitive membrane;

an odor specifier to specify the odor of the gas based on the reaction value of the sensitive membrane, detected by the substance sensor;

a reaction value calculator to calculate a reaction value corresponding to the odor specified by the odor specifier based on the reaction value of the sensitive membrane, detected by the substance sensor;

a percentage calculator to calculate a percentage of the reaction value corresponding to the odor specified by the odor specifier to a total of the reaction value corresponding to the odor, calculated by the reaction value calculator; and a display to display the percentage of the reaction value corresponding to the odor, calculated by the percentage calculator, so that comparison of the percentage is enabled in the odor specified by the odor specifier.

In such a case, it is also acceptable that:

the display displays the reaction value corresponding to the odor, calculated by the reaction value calculator, so that comparison of the reaction value is enabled in the odor specified by the odor specifier.

It is also acceptable that:

the display displays the reaction value corresponding to the odor, calculated by the reaction value calculator, and the percentage of the reaction value corresponding to the odor, calculated by the percentage calculator, so that comparison between the reaction value and the percentage is enabled.

It is also acceptable to further include:

a storage to store the reaction value of the sensitive membrane, detected by the substance sensor, in correspondence with time of detection, wherein the display displays at least one of the reaction value corresponding to the odor, calculated by the reaction value calculator, and the percentage of the reaction value corresponding to the odor, calculated by the percentage calculator, so that comparison of the at least one between different detection points is enabled, based on the reaction value of the sensitive membrane, stored in the storage.

An odor detection system according to a second aspect of the present disclosure includes:

a substance sensor including a sensitive membrane to react with a substance included in an odor of a gas in correspondence with the substance, the substance sensor being configured to detect a reaction value of the sensitive membrane;

a coefficient corrector to correct the reaction value of the sensitive membrane, detected by the substance sensor, in correspondence with the sensitive membrane, with a coefficient corresponding to the sensitive membrane, set depending on a condition of an environment surrounding the sensitive membrane; and an odor specifier to specify the odor of the gas based on the reaction value of the sensitive membrane, corrected by the coefficient corrector.

In such a case, it is also acceptable to further include:

a reaction value calculator to calculate a reaction value corresponding to the odor specified by the odor specifier based on the reaction value of the sensitive membrane, corrected by the coefficient corrector; and a display to display the reaction value corresponding to the odor, calculated by the reaction value calculator, so that comparison of the reaction value is enabled in the odor specified by the odor specifier.

It is also acceptable to further include:

a percentage calculator to calculate a percentage of the reaction value corresponding to the odor specified by the odor specifier to a total of the reaction value corresponding to the odor, calculated by the reaction value calculator, wherein the display displays the percentage of the reaction value corresponding to the odor, calculated by the percentage calculator, so that comparison of the percentage is enabled in the odor specified by the odor specifier.

It is also acceptable that:

the display displays the reaction value corresponding to the odor, calculated by the reaction value calculator, and the percentage of the reaction value corresponding to the odor, calculated by the percentage calculator, so that comparison between the reaction value and the percentage is enabled.

It is also acceptable to further include:

a storage to store the reaction value of the sensitive membrane, detected by the substance sensor, in correspondence with time of detection, wherein the display displays at least one of the reaction value corresponding to the odor, calculated by the reaction value calculator, and the percentage of the reaction value corresponding to the odor, calculated by the percentage calculator, so that comparison of the at least one between different detection points is enabled, based on the reaction value of the sensitive membrane, stored in the storage.

It is also acceptable to further include:

an environmental sensor to detect the condition of the environment, wherein the coefficient corrector corrects the reaction value of the sensitive membrane, detected by the substance sensor, in correspondence with the sensitive membrane, with a coefficient corresponding to the sensitive membrane, set depending on the condition of the environment, detected by the environmental sensor.

It is also acceptable that:

the condition of the environment includes at least one of a humidity, a temperature, and an air pressure.

An odor detection method according to a third aspect of the present disclosure is an odor detection method to be executed by an odor detection system to detect an odor of a gas, the odor detection method including:

specifying the odor of the gas based on a reaction value of a sensitive membrane, detected by a substance sensor including the sensitive membrane to react with a substance included in the odor of the gas in correspondence with the substance;

calculating a reaction value corresponding to the specified odor based on the reaction value of the sensitive membrane, detected by the substance sensor;

calculating a percentage of the reaction value corresponding to the specified odor to a total of the calculated reaction value corresponding to the odor; and displaying the calculated percentage of the reaction value corresponding to the odor so that comparison of the percentage is enabled in the specified odor.

An odor detection method according to a fourth aspect of the present disclosure is an odor detection method to be executed by an odor detection system to detect an odor of a gas, the odor detection method including:

correcting a reaction value of a sensitive membrane, detected by a substance sensor including the sensitive membrane to react with a substance included in the odor of the gas in correspondence with the substance, in correspondence with the sensitive membrane, with a coefficient corresponding to the sensitive membrane, set depending on a condition of an environment surrounding the sensitive membrane;

specifying the odor of the gas based on the corrected reaction value of the sensitive membrane;

calculating a reaction value corresponding to the specified odor based on the corrected reaction value of the sensitive membrane; and displaying the calculated reaction value corresponding to the odor so that comparison of the reaction value in the specified odors.

A program according to a fifth aspect of the present disclosure causes a computer to function as:

an odor specifier to specify an odor of a gas based on a reaction value of a sensitive membrane, detected by a substance sensor including the sensitive membrane to react with a substance included in the odor of the gas in correspondence with the substance;

a reaction value calculator to calculate a reaction value corresponding to the odor specified by the odor specifier based on the reaction value of the sensitive membrane, detected by the substance sensor;

a percentage calculator to calculate a percentage of the reaction value corresponding to the odor specified by the odor specifier to a total of the reaction value corresponding to the odor, calculated by the reaction value calculator; and a display to display the percentage of the reaction value corresponding to the odor, calculated by the percentage calculator, so that comparison of the percentage is enabled in the odor specified by the odor specifier.

A program according to a sixth aspect of the present disclosure causes a computer to function as:

a coefficient corrector to correct a reaction value of a sensitive membrane, detected by a substance sensor including the sensitive membrane to react with a substance included in an odor of a gas in correspondence with the substance, in correspondence with the sensitive membrane, with a coefficient corresponding to the sensitive membrane, set depending on a condition of an environment surrounding the sensitive membrane;

an odor specifier to specify the odor of the gas based on the reaction value of the sensitive membrane, corrected by the coefficient corrector;

a reaction value calculator to calculate a reaction value corresponding to the odor specified by the odor specifier based on the reaction value of the sensitive membrane, corrected by the coefficient corrector; and a display to display the reaction value corresponding to the odor, calculated by the reaction value calculator, so that comparison of the reaction value is enabled in the odor specified by the odor specifier.

Advantageous Effects of Invention

In accordance with the present disclosure, variations in the results of detection of an odor can be reduced regardless of the number of measurements or the condition of an environment.

BRIEF DESCRIPTION OF DRAWINGS

FIG. 6A is a view illustrating an example of a bar graph indicating the first and second measurement results compared based on an absolute amount;

FIG. 15 is a flow chart illustrating detection processing in the odor detection system in FIG. 12.

DESCRIPTION OF EMBODIMENTS

Figure 1:
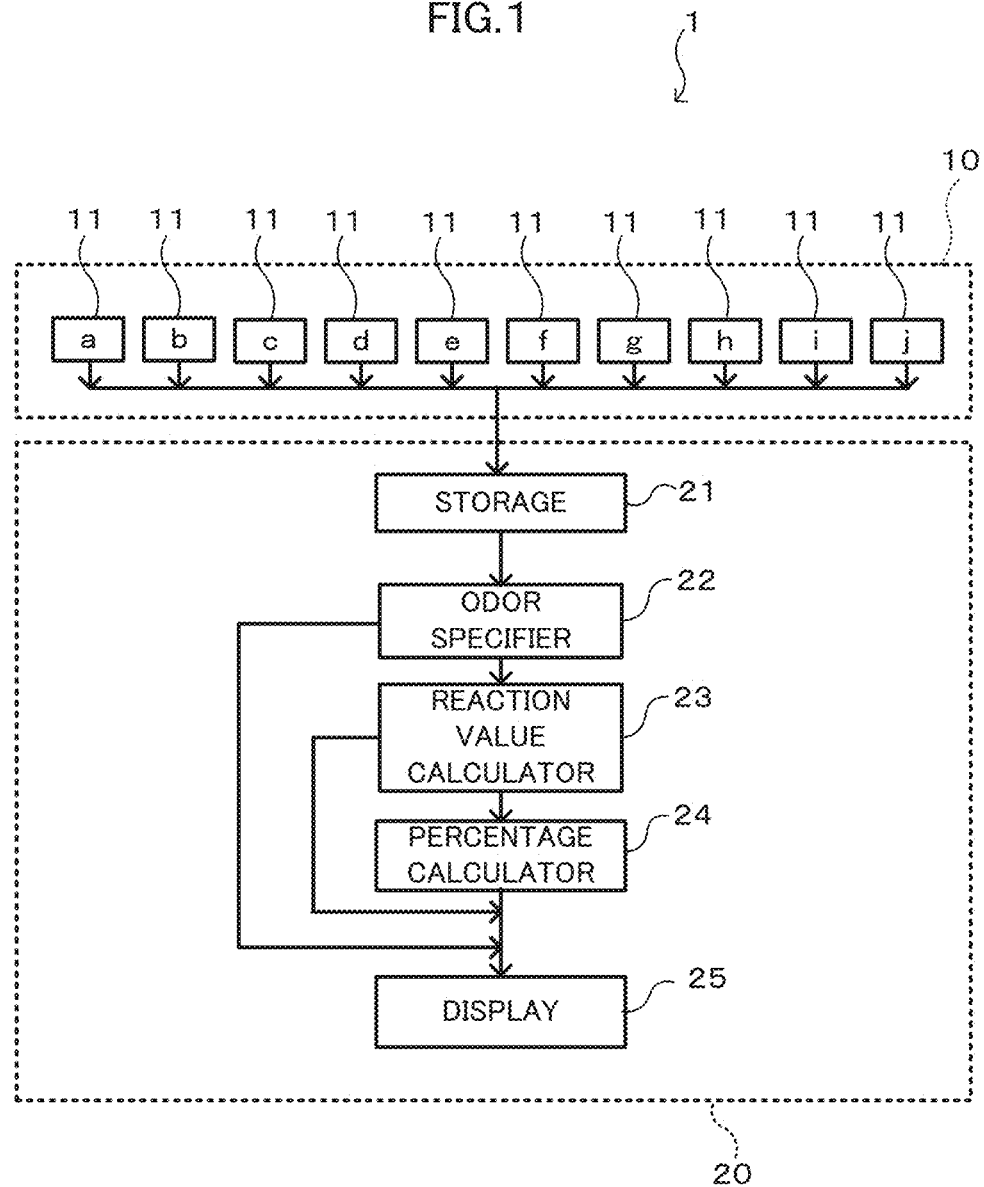
FIG. 1 is a block diagram illustrating the configuration of an odor detection system according to Embodiment 1 of the present disclosure.

Embodiments of the present disclosure are described in detail below with reference to the drawings. In each drawing, the same or similar portions are denoted by the same reference characters.

Embodiment 1

First, Embodiment 1 of the present disclosure is described. As illustrated in FIG. 1, an odor detection system 1 includes a substance sensor 10 and an information-processing device 20. The odor detection system 1 detects a plurality of substances a to j included in the odor of a gas.

The substance sensor 10 includes, in correspondence with the substances a to j, sensitive membranes 11 to react with the substances a to j, respectively. Hereinafter, the sensitive membranes 11 are also referred to as sensitive membranes a to j corresponding to the substances a to j, with which the sensitive membranes a to j react, respectively. The substance sensor 10 detects the reaction values of the sensitive membranes a to j, and outputs signals indicating the detected reaction values.

The information-processing device 20 performs information processing for detecting the odor of a gas. The information-processing device 20 includes a storage 21, an odor specifier 22, a reaction value calculator 23, a percentage calculator 24, and a display 25.

Figure 2:
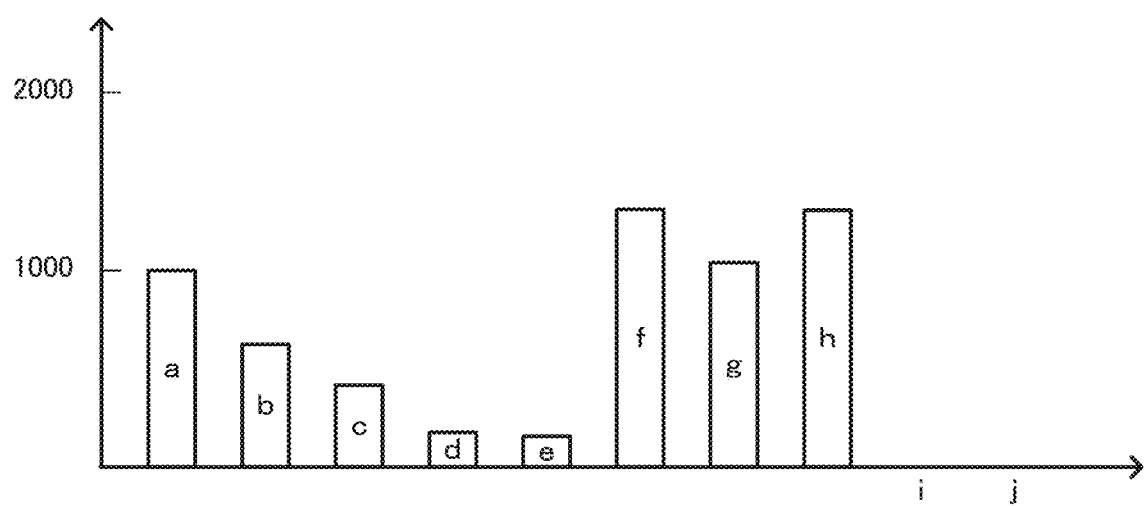
FIG. 2 is a view illustrating an example of the pattern of the reaction values of sensitive membranes, detected by a substance sensor included in the odor detection system in FIG. 1.

The storage 21 stores the reaction values of the sensitive membranes a to j, detected by the substance sensor 10, in correspondence with time of the detection whenever the reaction values are detected. The storage 21 stores the reaction values of the sensitive membranes a to j to react with the substances a to j, output from the substance sensor 10, for example, in association with time (points of detection) at which the reaction values are detected. The reaction values of the sensitive membranes 11 to react with the substances a to j have a pattern, for example, as illustrated in FIG. 2. The reaction value of the ordinate of FIG. 2 indicates the signal level of a detection signal from the substance sensor 10, changed by reaction of each sensitive membrane 11 with each substance in the substance sensor 10.

Referring back to FIG. 1, the odor specifier 22 specifies an odor included in a gas on the basis of the reaction values of the sensitive membranes a to j, detected by the substance sensor 10 and stored in the storage 21. For example, it is assumed that an odor A consists of substances a, b, and c, an odor B consists of substances d and e, and an odor C consists of substances f, g, and h. It is assumed that the odor specifier 22 stores the pattern for reference of the reaction values of the substances a, b, and c of the odor A, the pattern for reference of the reaction values of the substances d and e of the odor B, and the pattern for reference of the reaction values of the substances f, g, and h of the odor C.

The odor specifier 22 specifies the odor included in the gas by determining whether or not the pattern of the detected reaction values of the substances, illustrated in FIG. 2, corresponds to the pattern of the odor A, corresponds to the pattern of the odor B, or corresponds to the pattern of the odor C, on the basis of the reaction values of the sensitive membranes a to j, stored in the storage 21. Specifically, the odor specifier 22 performs comparison between the percentages of the reaction values of the sensitive membranes a, b, and c related to the odor A and the pattern for reference of the percentages of the reaction values of the sensitive membranes a, b, and c for the odor A, to determine whether or not the odor A is included in the gas. Moreover, the odor specifier 22 performs comparison between the percentages of the reaction values of the sensitive membranes d and e related to the odor B and the pattern for reference of the percentages of the reaction values of the sensitive membranes d and e for the odor B, to determine whether or not the odor B is included in the gas. Moreover, the odor specifier 22 performs comparison between the percentages of the reaction values of the sensitive membranes f, g, and h related to the odor C and the pattern for reference of the percentages of the reaction values of the sensitive membranes f, g, and h for the odor C, to determine whether or not the odor C is included in the gas. Descriptions are made on the assumption that the pattern of the reaction values illustrated in FIG. 2 corresponds to the pattern of the odors A, B, and C, and that the odors A, B, and C are specified.

Figure 3:
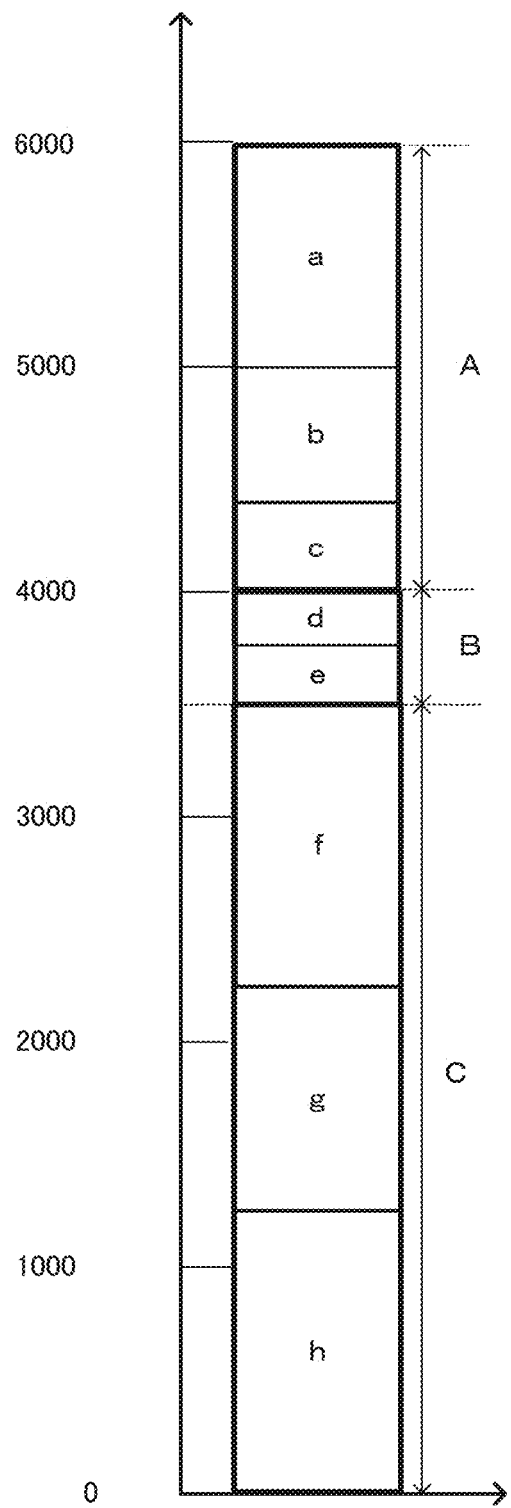
FIG. 3 is a view illustrating an example of a bar graph collectively indicating the reaction values of sensitive membranes in correspondence with odors.
Figure 4:
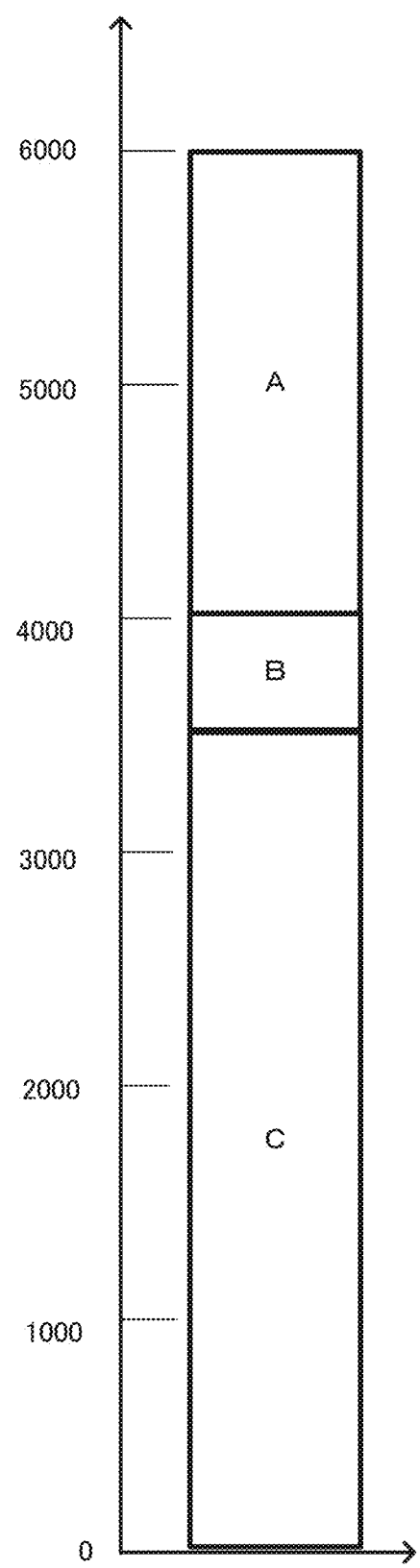
FIG. 4 is a view illustrating an example of a bar graph indicating reaction values corresponding to specified odors, compared between the odors.

Referring back to FIG. 1, the reaction value calculator 23 calculates reaction values corresponding to the odors specified by the odor specifier 22 on the basis of the reaction values of the sensitive membranes a to j, detected by the substance sensor 10. Specifically, the reaction value calculator 23 calculates, as the reaction values corresponding to the odors, the total values, corresponding to the odors, of the reaction values of the sensitive membranes a to j. For example, as illustrated in FIG. 3, the reaction value calculator 23 adds the reaction values of the substances a, b, and c related to the odor A to calculate the total value of the reaction values, adds the reaction values of the substances d and e related to the odor B to calculate the total value of the reaction values, and adds the reaction values of the substances f, g, and h related to the odor C to calculate the total value of the reaction values. FIG. 4 collectively indicates the total values as the reaction values corresponding to the odors.

The reaction values corresponding to the odors are not limited to the total values of the reaction values of the sensitive membranes 11. The reaction values may be the average values of the reaction values of the sensitive membranes 11. The reaction values corresponding to the odors may be preferably representative values representing the levels of the reaction values of the sensitive membranes 11 with which the substances included in the odors react.

Referring back to FIG. 1, the percentage calculator 24 calculates the percentages of the reaction values corresponding to the odors specified by the odor specifier 22 to the totals of the reaction values corresponding to the odors, calculated by the reaction value calculator 23. For example, the percentage calculator 24 converts the reaction values of the odors A, B, and C, indicated in FIG. 4 into the percentages of the reaction values of the odors A, B, and C to the total of all the reaction values indicated in FIG. 5.

Figure 5:
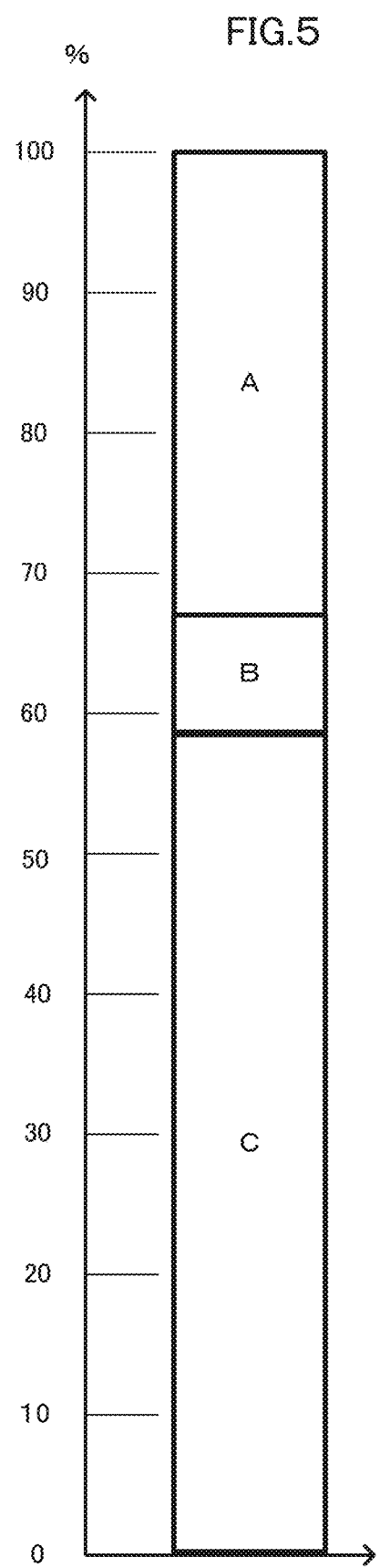
FIG. 5 is a view illustrating an example of a bar graph indicating the percentages of the reaction values of the specified odors, compared between the odors.

Referring back to FIG. 1, the display 25 displays the percentages of the reaction values corresponding to the odors, calculated by the percentage calculator 24, so that comparison of the percentages is enabled between the odors specified by the odor specifier 22. For example, the display 25 displays a bar graph as illustrated in FIG. 5. The bar graph enables comparison of the percentages of the odors A, B, and C of the gas to the total.

The display 25 can also display another content. For example, the display 25 can display the reaction values corresponding to the odors, calculated by the reaction value calculator 23, so that comparison of the reaction values is enabled between the odors specified by the odor specifier 22. For example, the display 25 displays a bar graph as illustrated in FIG. 4. The bar graph enables comparison of the reaction values of the odors A, B, and C of the gas between the odors A, B, and C.

Further, the display 25 can display the reaction values corresponding to the odors, calculated by the reaction value calculator 23, and the percentages of the reaction values corresponding to the odors, calculated by the percentage calculator 24, so that comparison of the reaction values and the percentages is enabled. The display 25 displays, for example, the bar graph that is illustrated in FIG. 4 and indicates the reaction values corresponding to the odors A, B, and C, and the bar graph that is illustrated in FIG. 5 and indicates the percentages of the reaction values corresponding to the odors A, B, and C, so that comparison of the bar graphs is enabled.

Figure 6B:
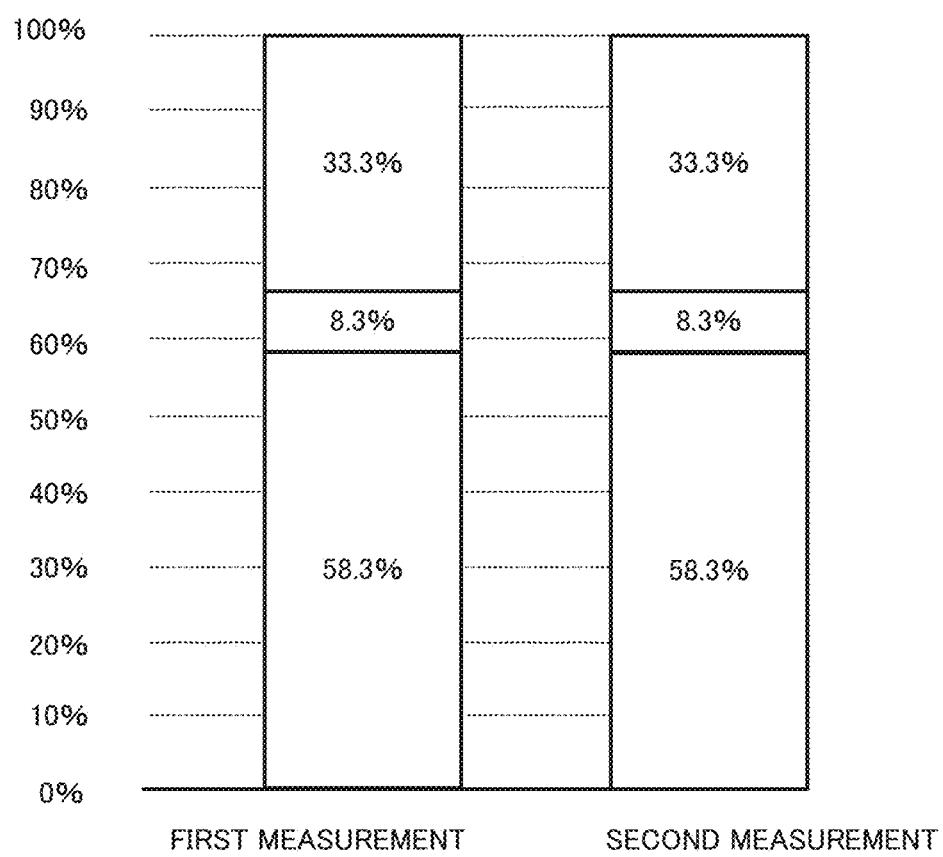
FIG. 6B is a view illustrating an example of a bar graph indicating the first and second measurement results compared based on a percentage.

Further, the display 25 can display at least one of the reaction values corresponding to the odors, calculated by the reaction value calculator 23, and the percentages of the reaction values corresponding to the odors, calculated by the percentage calculator 24, so that comparison of the at least one between different detection points is enabled, on the basis of the reaction values of the sensitive membranes a to j, stored in the storage 21. For example, the display 25 is capable of performing comparative display of reaction values corresponding to the odors A, B, and C in the first and second measurements for gases containing the same constituents, as illustrated in FIG. 6A. Moreover, the display 25 is capable of performing comparative display of the percentages of the reaction values corresponding to the odors A, B, and C in the first and second measurements for gases containing the same constituents, as illustrated in FIG. 6B. Further, the display 25 can simultaneously perform the comparative display illustrated in FIG. 6A and the comparative display illustrated in FIG. 6B.

Performing such display enables recognition that the percentages of the odor A, B, or C in the first and second measurements were equal in comparison between the first and second measurements in the case of the conversion into the percentages of the reaction values corresponding to the odors although the sensitivities of the sensitive membranes 11 and the reaction values corresponding to the odors A, B, and C in the second measurement are less than those in the first measurement.

The number of different detection points between which comparison is performed is not limited to two. Comparison between three or more detection points is also possible.

Figure 7:
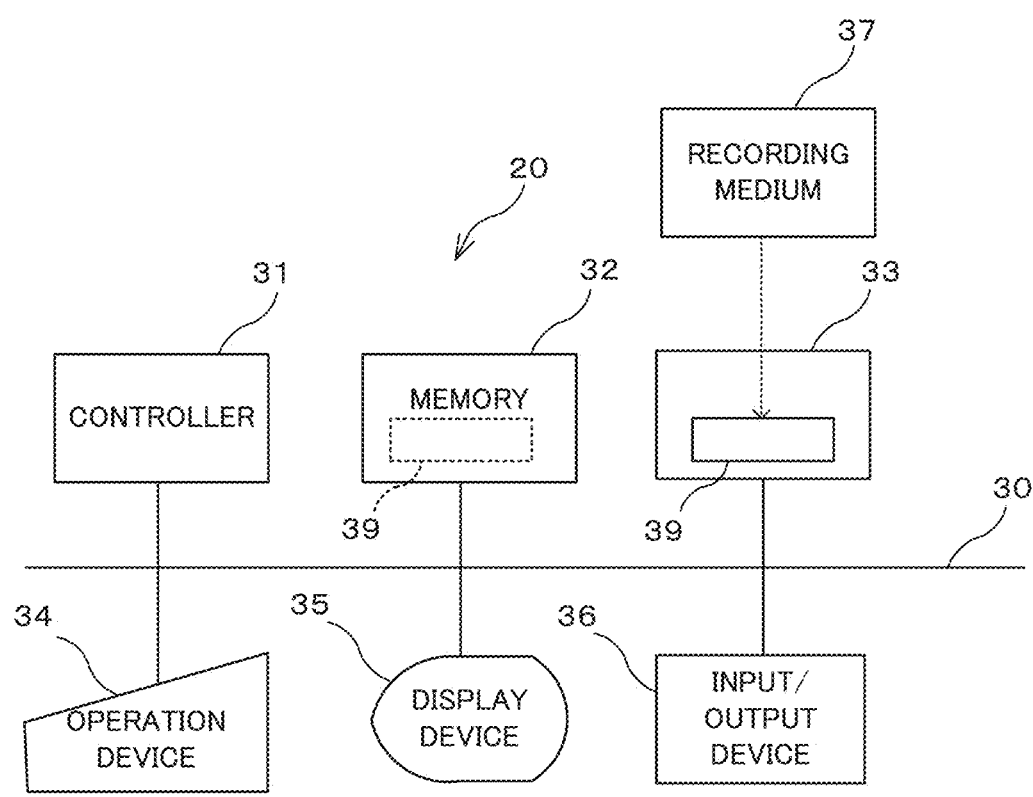
FIG. 7 is a block diagram illustrating the hardware configuration of an information-processing device included in the odor detection system in FIG. 1.

The function of the information-processing device 20 of the odor detection system 1 described above is implemented by hardware configurations illustrated in FIG. 7. As illustrated in FIG. 7, the odor detection system 1 includes a controller 31, a memory 32, an external storage 33, an operation device 34, a display device 35, and an input/output device 36 as the hardware configurations. All of the memory 32, the external storage 33, the operation device 34, the display device 35, and the input/output device 36 are connected to the controller 31 through an internal bus 30.

The controller 31 includes a central processing unit (CPU). The CPU executes processing in accordance with a program 39 stored in the external storage 33, to thereby implement each component of the odor detection system 1 illustrated in FIG. 1.

The memory 32 includes random-access memory (RAM). The program 39 stored in the external storage 33 is loaded into the RAM of the memory 32. The CPU executes the program 39 loaded into the RAM. In addition, the memory 32 is used as a work area (temporary storage area for data) for the controller 31.

The external storage 33 includes a nonvolatile memory such as a flash memory, a hard disk, a digital versatile disc random-access memory (DVD-RAM), or a digital versatile disc rewritable (DVD-RW). The program 39 to be executed by the controller 31 is stored in advance in the nonvolatile memory of the external storage 33, and the program 39 is read in the memory 32. In accordance with an instruction provided by the controller 31, the external storage 33 supplies data to be used when the program 39 is executed, to the controller 31, and stores data supplied from the controller 31.

In the present embodiment, the storage 21, odor specifier 22, reaction value calculator 23, and percentage calculator 24 of the odor detection system 1 correspond to the controller 31, the memory 32, and the external storage 33.

The operation device 34 is a man-machine interface to be operated by an operator. The operation device 34 includes a keyboard, a pointing device such as a mouse, and a keyboard. An operated input into the operation device 34 is transmitted to the controller 31. The controller 31 executes the program 39 in accordance with the content of the operated input.

The display device 35 is a man-machine interface to display an image. The display device 35 includes a cathode ray tube (CRT) or a liquid crystal display (LCD). The display device 35 displays at least one of the reaction value of a detected odor and the percentage of the reaction value of the odor. The display device 35 corresponds to the display 25. The operation device 34 and the display device 35 may be unified into a single touch panel.

The input/output device 36 is an interface that can input and output information into and from the substance sensor 10. Through the input/output device 36, a detection instruction for the substance sensor 10 is output, and a signal indicating the reaction value of each sensitive membrane 11 from the substance sensor 10 is input.

The external storage 33 can be connected to a non-transitory recording medium 37. The program 39 is stored in the recording medium 37. The program 39 may be configured to be transferred from the recording medium 37 to the external storage 33, and to be written in the external storage 33.

Processing in the odor detection system 1 according to Embodiment 1 of the present disclosure, that is, an odor detection method to be executed by the odor detection system 1 to detect the odor of a gas is now described. The processing is classified roughly into: detection processing of detecting the reaction values of the sensitive membranes a to j by allowing the substance sensor 10 to perform the detection; and analytical display processing of an odor, based on the reaction values of the sensitive membranes a to j, detected by the substance sensor 10.

(Detection Processing)

Figure 8:
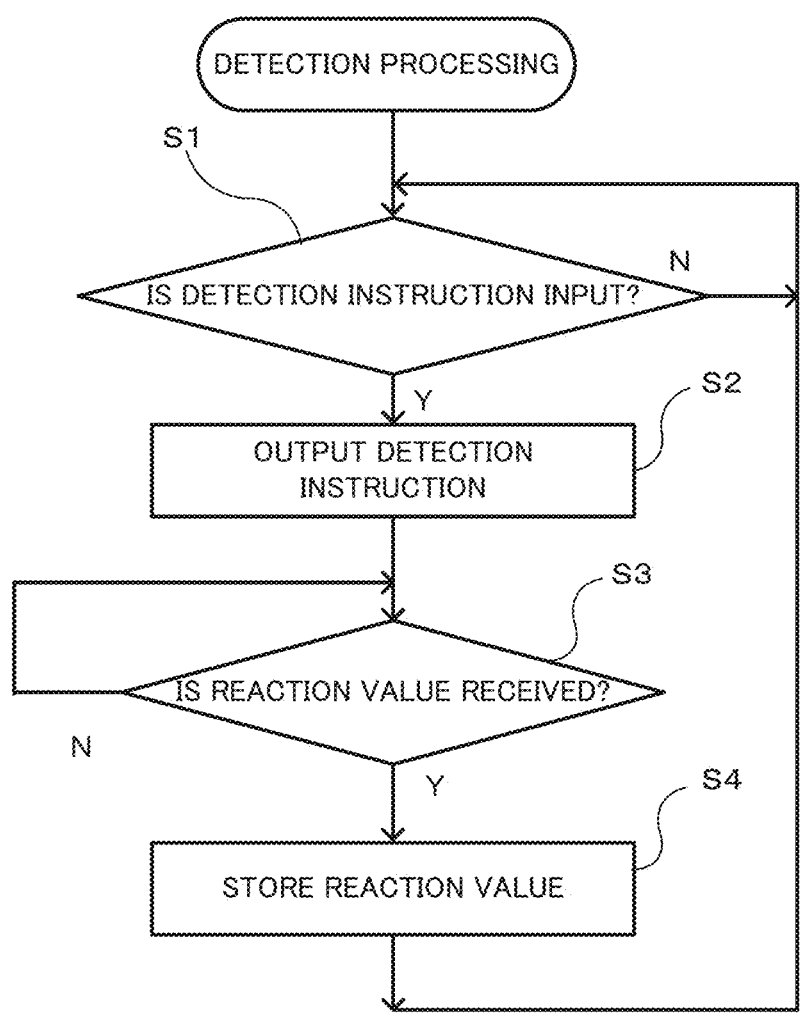
FIG. 8 is a flow chart illustrating detection processing in the odor detection system in FIG. 1.

First, the detection processing is described. As illustrated in FIG. 8, the information-processing device 20 waits until a detection instruction is input by an operated input (step S1; No). Specifically, the controller 31 waits for the detection instruction by the input operated by the operation device 34, as illustrated in FIG. 7.

When the detection instruction is input by the operated input (step S1; Yes), the information-processing device 20 outputs the detection instruction to the substance sensor 10 (step S2). Specifically, the controller 31 outputs the detection instruction to the substance sensor 10 through the input/output device 36 when the input operated by the operation device 34 is the detection instruction, as illustrated in FIG. 7. The substance sensor 10 detects the substances a to j included in the gas, and outputs a signal indicating the reaction value of each of the sensitive membranes a to j to the input/output device 36. The input/output device 36 converts the signals into the data of the reaction values, and supplies the data to the controller 31. As described above, steps S1 and S2 correspond to a detection step in the present embodiment.

During this period, the information-processing device 20 waits until a reaction value is received (step S3; No). When the reaction value is received (step S3; Yes), the storage 21 stores the reaction value (step S4). Specifically, the controller 31 associates the reaction value with detection time, and allows the reaction value to be stored in the external storage 33, as illustrated in FIG. 7.

After step S4, the information-processing device 20 goes back to step S1. Thereafter, whenever steps S1 to S4 are repeated, the substance sensor 10 detects the reaction values of the sensitive membranes a to j, and the storage 21 stores the reaction values of the sensitive membranes a to j, associated with the detection time. The detection processing is performed in such a manner.

(Analytical Display Processing)

Figure 9:
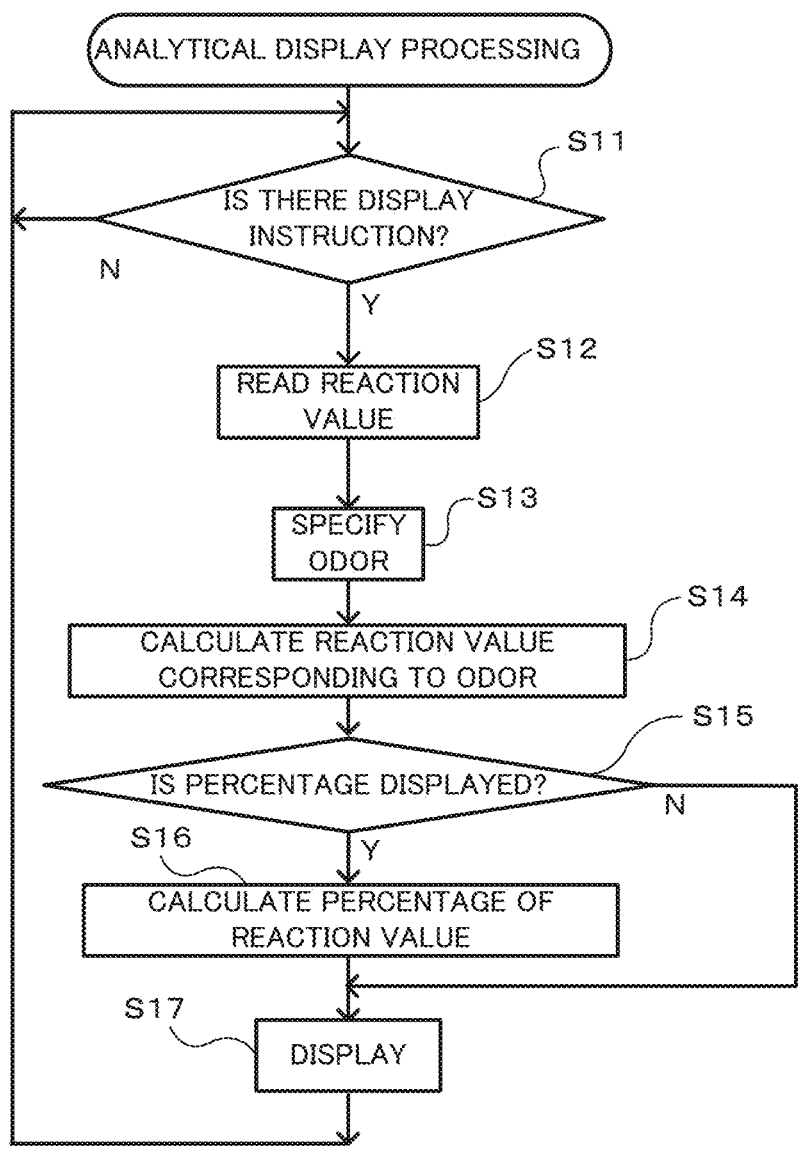
FIG. 9 is a flow chart illustrating analytical display processing in the odor detection system in FIG. 1.

The analytical display processing is now described. As illustrated in FIG. 9, first, the information-processing device 20 waits until a display instruction is input (step S11; No). As illustrated in FIG. 7, the controller 31 waits for the display instruction input operated by the operation device 34. Detection time is designated in the display instruction. When no detection time is designated, the latest reaction values of the sensitive membranes a to j are targeted for analysis.

When the display instruction is input by the input operated by the operation device 34 (step S11; Yes), the odor specifier 22 reads the reaction values at the detection time designated in the display instruction from the storage 21 (step S12). Specifically, the controller 31 reads the reaction values of the sensitive membranes a to j at the designated detection time from the external storage 33 into the memory 32, as illustrated in FIG. 7. The controller 31 reads the pattern for reference of the reaction values of the odors A, B, C, . . . from the external storage 33 into the memory 32.

Subsequently, the odor specifier 22 specifies the odor of the gas on the basis of the read reaction values of the sensitive membranes a to j at the detection time (step S13; odor specific step). Specifically, the controller 31 compares the pattern of the reaction values of the sensitive membranes a to j, read into the memory 32, and the pattern for reference of the reaction values corresponding to the odors to specify the odor included in the gas, as illustrated in FIG. 7. For example, as illustrated in FIG. 3, the odor A is specified based on the pattern of the reaction values of the substances a, b, and c, the odor B is specified based on the pattern of the reaction values of the substances d and e, and the odor C is specified based on the pattern of the reaction values of the substances f, g, and h.

Subsequently, the reaction value calculator 23 calculates the reaction value corresponding to the odor specified in step S13 on the basis of the reaction values of the sensitive membranes a to j (step S14; reaction value calculation step). Specifically, as illustrated in FIG. 7, the controller 31 calculates the total values of the reaction values of the sensitive membranes a to j, stored in the memory 32, in correspondence with the odors, and allows the total values to be stored as the reaction values corresponding to the odors in the memory 32. For example, as illustrated in FIG. 3, the reaction values of the substances a, b, and c are added up for the odor A to calculate the reaction value of the odor A, the reaction values of the substances d and e are added up for the odor B to calculate the reaction value of the odor B, and the reaction values of the substances f, g, and h are added up for the odor C to calculate the reaction value of the odor C.

Further, the percentage calculator 24 determines whether or not the percentage of the reaction value corresponding to the odor is displayed (step S15). When the percentage of the reaction value corresponding to the odor is displayed (step S15; Yes), the percentage calculator 24 calculates the percentage of the reaction value corresponding to the odor specified in step S13 to the total of the reaction values corresponding to the odors, calculated in step S14 (step S16; percentage calculation step). Specifically, as illustrated in FIG. 7, the controller 31 reads the reaction values corresponding to the odors, read from the memory 32, into the memory 32 to calculate the total of the reaction values, calculates the percentage of the reaction value corresponding to the odor to the total, and allows the percentage to be stored in the memory 32. Herein, for example, as illustrated in FIG. 5, the percentages of the odor A, the odor B, and the odor C are calculated.

Then, the display 25 performs display (step S17; display step). Specifically, as illustrated in FIG. 7, the controller 31 allows the bar graph illustrated in FIG. 2, 3, 4, 5, 6A, or 6B to be displayed on the display device 35 on the basis of the reaction values corresponding to the odors, calculated in the memory 32, or the percentages of the reaction values, in accordance with a designated content, in response to the display instruction described above. As a result, comparative display of the percentages of the reaction values corresponding to the odors between the odors is enabled.

After step S17, the processing in the information-processing device 20 returns to step S11. In such a manner, the analytical display processing is executed.

Figure 10A:
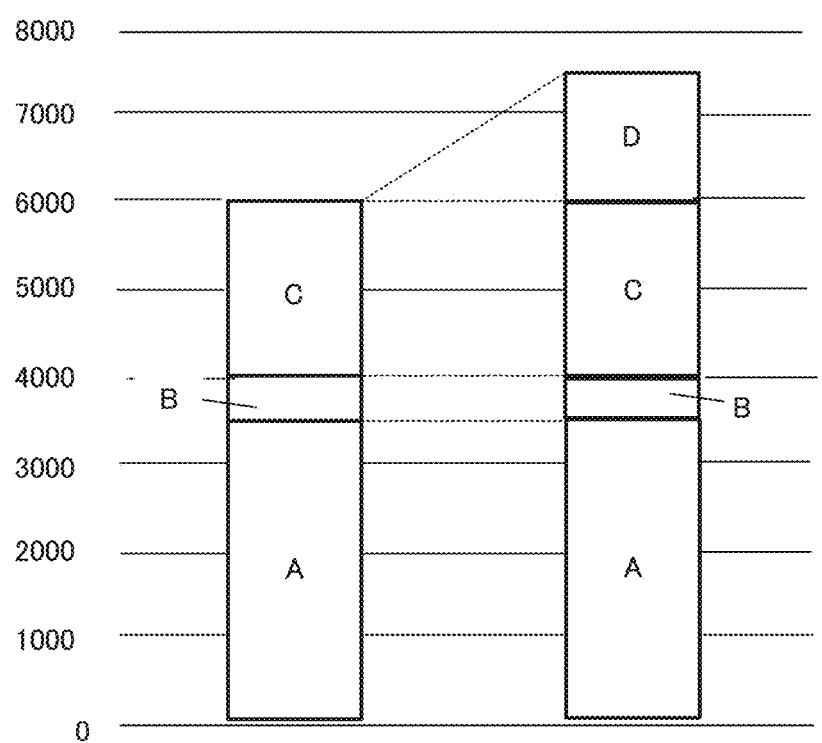
FIG. 10A is a graph indicating an example of data that can be analyzed.
Figure 10B:
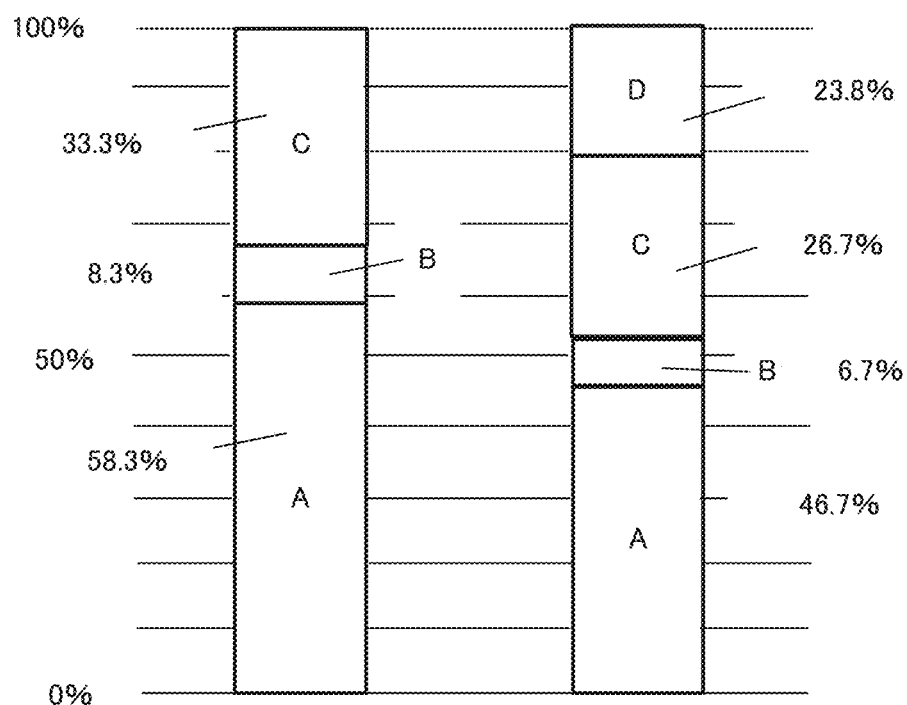
FIG. 10B is a graph indicating an example of data that can be analyzed.

In accordance with the odor detection system 1, an odor included in a gas can be analyzed from various aspects. For example, when an odor D (for example, mint) is newly added in the case of detecting a mouth odor, and detecting an odor A (for example, garlic), an odor B (for example, alcohol), and an odor C (for example, tobacco), it is difficult to recognize the effect of the odor D because display of reaction values illustrated in FIG. 10A merely shows that only the odor D is added. In contrast, as a result of conversion into the percentages of reaction values corresponding to the odors and display the percentages of the reaction values corresponding to the odors as illustrated in FIG. 10B, the inclusion of the odor D in the mouth odor is found to result in decreases in the percentages of the reaction values of the other odors A, B, and C, and therefore, the display enables recognition that the uncomfortable smells can be reduced.

Figure 11A:
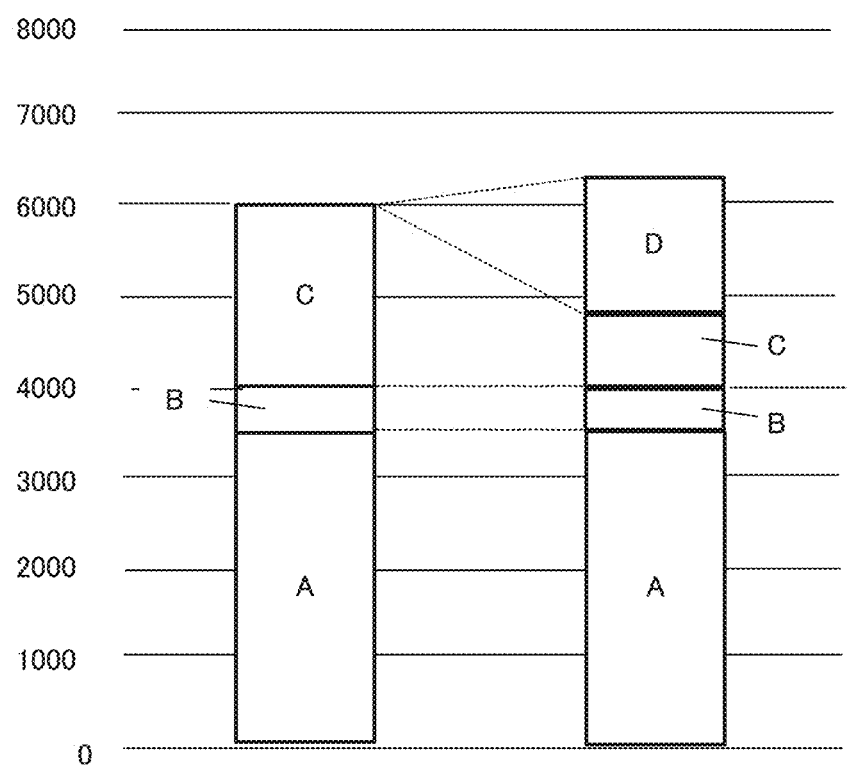
FIG. 11A is a graph indicating another example of data that can be analyzed.
Figure 11B:
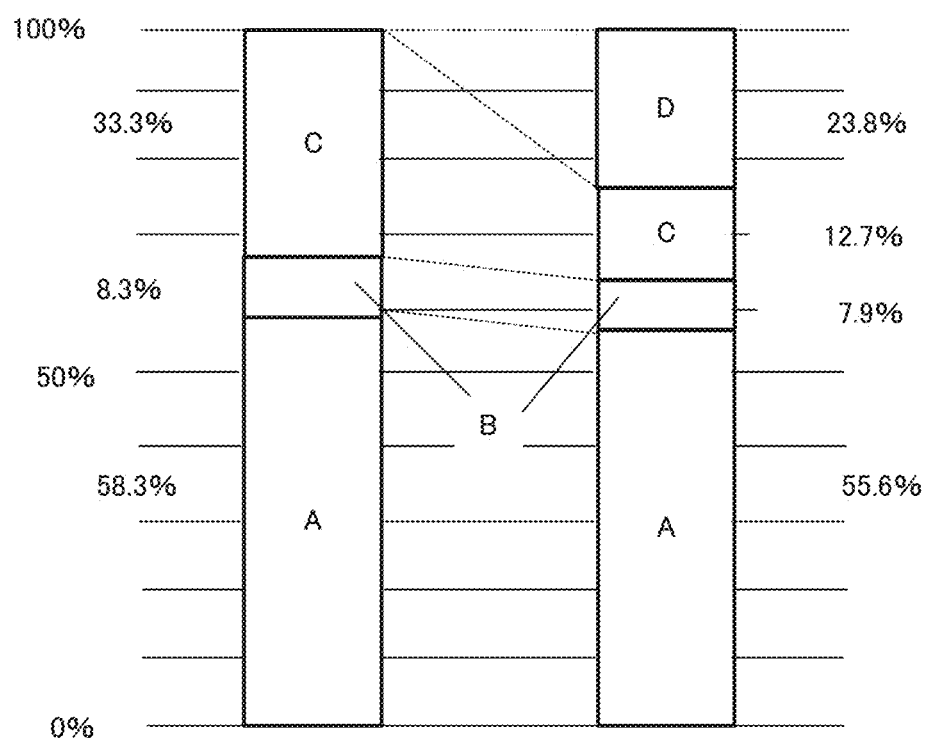
FIG. 11B is a graph indicating another example of data that can be analyzed.

Both display of reaction values in FIG. 11A and display of the percentages of the reaction values in FIG. 11B reveal that an odor C is reduced when an odor D (for example, mint) is newly added in the case of detecting a mouth odor and detecting an odor A (for example, garlic), an odor B (for example, alcohol), and the odor C (for example, tobacco). In comparison between FIGS. 11A and 11B, however, the display of the percentages of the reaction values corresponding to the odors, illustrated in FIG. 11B, more easily allows confirmation that the addition of the odor D results in a great decrease in the percentage of the odor C.

In the present embodiment, the detection processing and the analytical display processing are processing based on an event driven method, in which detection and analytical display can be separately performed. However, the detection processing and the analytical display processing may be processing in series.

As described above, the function of the information-processing device 20 is implemented by allowing the hardware resources illustrated in FIG. 7 to execute the detection processing program illustrated in FIG. 8 and the analytical display processing program illustrated in FIG. 9.

As described in detail above, variations in the detection results of the odors A, B, C, . . . can be reduced because the accurate percentages of the odors included in the gas can be determined regardless of a change in the sensitivities of the sensitive membranes 11 depending on the number of measurements, in accordance with the present embodiment. Changes in the percentages of the odors due to addition or reduction of a new odor (FIGS. 10A and 10B) and the influence of the addition or reduction of the new odor on the other odors (FIGS. 11A and 11B) can be analyzed when the variations in the detection results of the odors A, B, C, . . . can be reduced.

The odor detection system 1 according to the present embodiment may be configured to display only the percentages of the reaction values corresponding to the odors rather than to display the reaction values corresponding to the odors. In such a case, the determination in step S15 is not performed.

Embodiment 2

Figure 12:
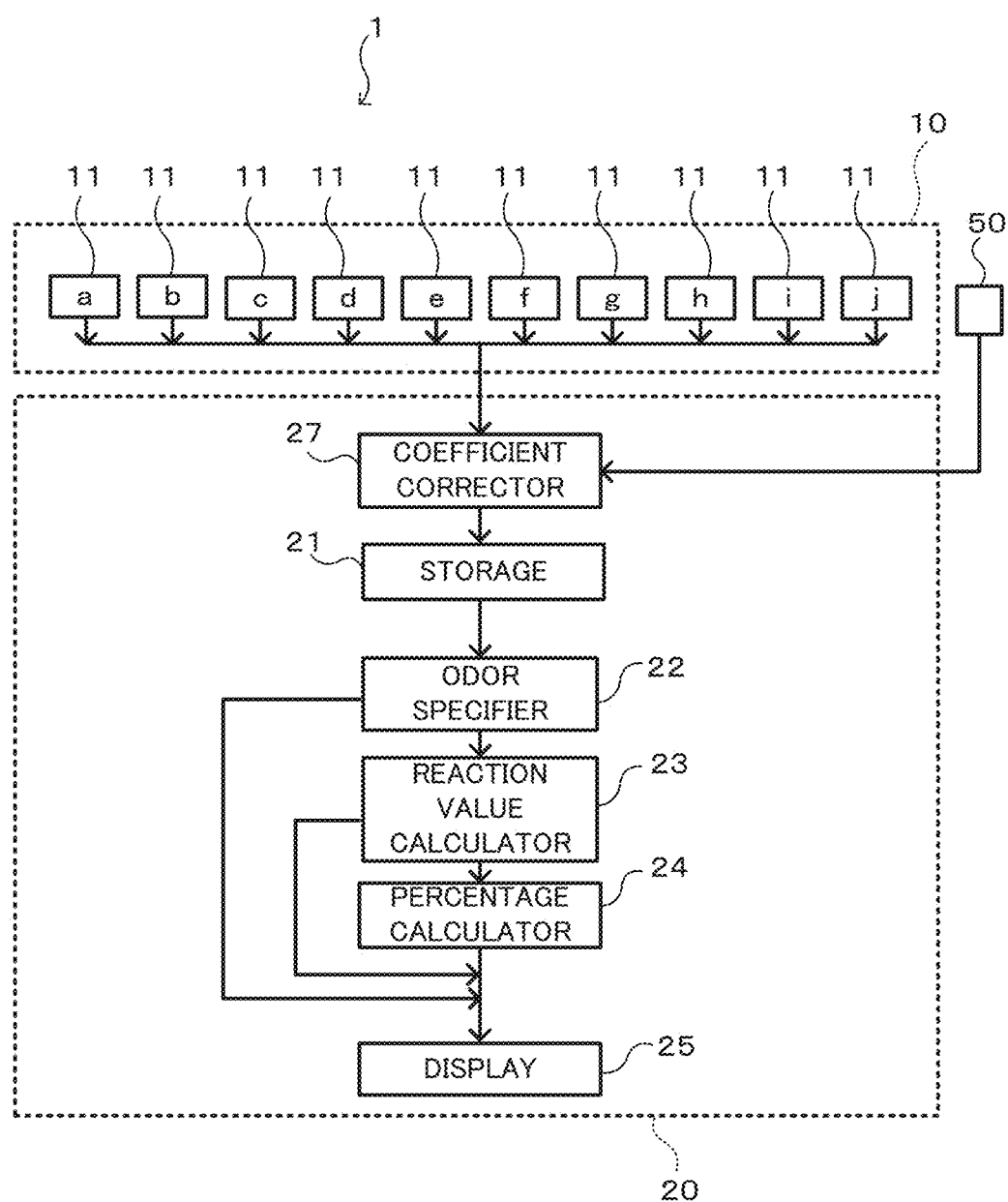
FIG. 12 is a block diagram illustrating the configuration of an odor detection system according to Embodiment 2 of the present disclosure.

Embodiment 2 of the present disclosure is now described. As illustrated in FIG. 12, an odor detection system 1 according to the present embodiment is different from the odor detection system 1 according to Embodiment 1 described above in that an information-processing device 20 includes a coefficient corrector 27 and in that the odor detection system 1 includes an environmental sensor 50. The environmental sensor 50 is connected to the information-processing device 20 through an input/output device 36, as illustrated in FIG. 7.

In the present embodiment, the odor detection system 1 includes the environmental sensor 50 to detect the environmental condition of a gas. In the present embodiment, the environmental condition to be detected by the environmental sensor 50 is a humidity. Examples of the humidity include humidities based on various standards. However, absolute humidity, relative humidity, or the like based on any standard may be used as the humidity.

Figure 13:
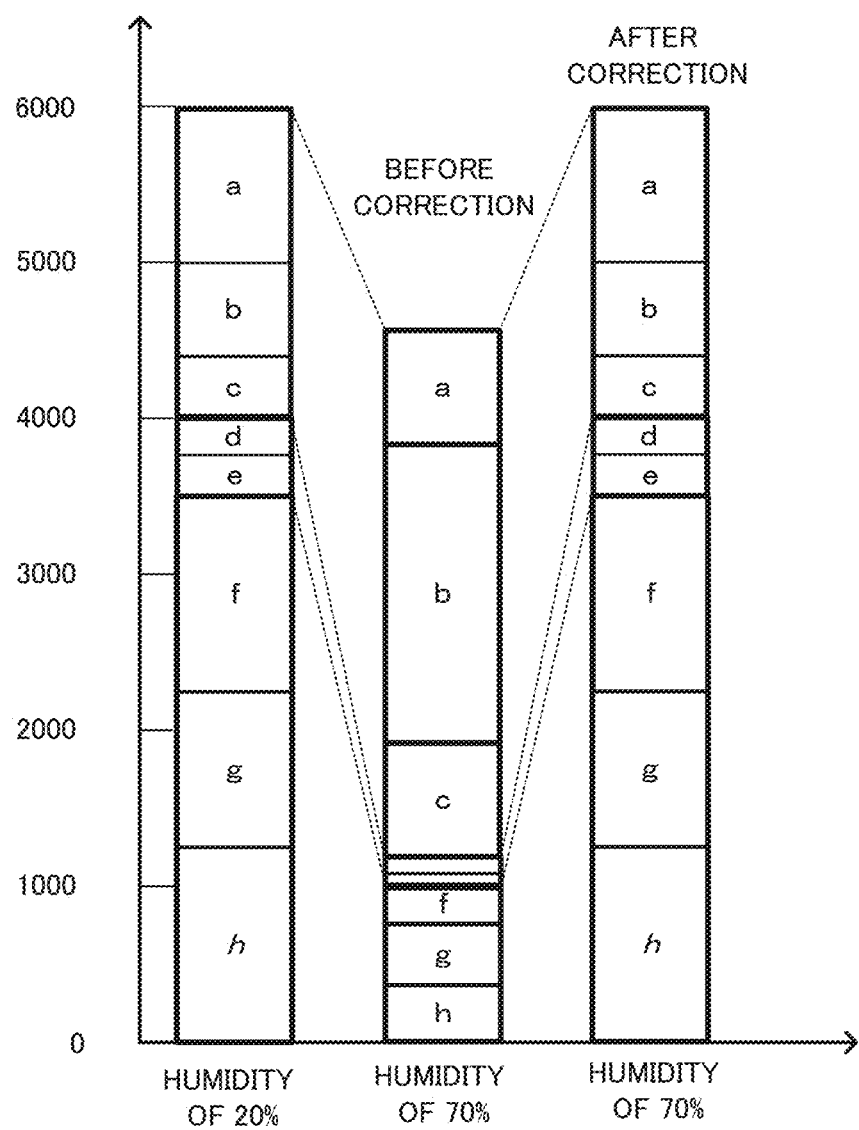
FIG. 13 is a view illustrating reaction values corresponding to odors at different humidities, and reaction values compared before and after correction.
Figure 14:
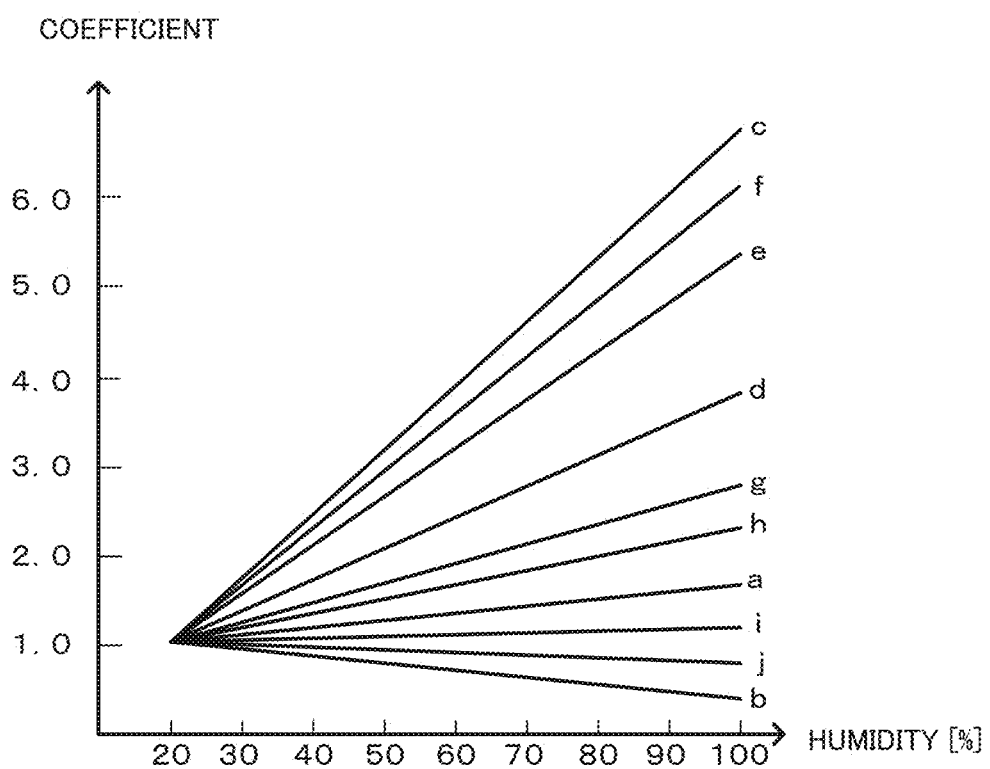
FIG. 14 is a graph indicating relationships between humidity and the coefficients of sensitive membranes.

The coefficient corrector 27 corrects the reaction values of sensitive membranes a to j, detected by a substance sensor 10, in correspondence with the sensitive membranes a to j, with coefficients corresponding to the sensitive membranes a to j, set depending on the condition of an environment surrounding the sensitive membranes a to j, detected by the environmental sensor 50. For example, with regard to the reaction values of the sensitive membranes a to j, the reaction values of the sensitive membranes a to j vary depending on the humidity even when the amounts of substances a to j included in the gas are equal, as illustrated in FIG. 13. Thus, the coefficient corrector 27 includes coefficients varying with humidity, as illustrated in FIG. 14, in correspondence with the sensitive membranes a to j, and multiplies the reaction values of the sensitive membranes a to j by the coefficient corresponding to the then detected humidity to correct the reaction values. As a result, for example, the reaction values corresponding to the sensitive membranes a to j at a humidity of 70% are as indicated by the bar graph of "AFTER CORRECTION" illustrated in FIG. 13. According to the bar graph, the reaction values of the sensitive membranes a to j at a humidity of 70% are equal to the reaction values of the sensitive membranes a to j at a humidity of 20%.

Conversely, the coefficients can be determined by detecting the reaction values of the sensitive membranes a to j while changing humidity for a gas with the same constituents, and comparing the reaction values at each humidity. In other words, calibration is enabled in such a manner. In such a case, for example, coefficients may be detected at humidities of 20% and 70%, and may be interpolated based on the detection results to determine each coefficient at the other humidities.

The coefficients illustrated in FIG. 14 are coefficients in a case in which the reaction values of the sensitive membranes a to j at a humidity of 20% are set to 1; however, the present disclosure is not limited thereto. For example, coefficients for the other sensitive membranes b to j in a case in which the reaction value of the sensitive membrane a is always set to 1 may be used. In the case of using such coefficients, the percentages of the reaction values of the sensitive membranes a to j can also be appropriately corrected to in turn precisely display the percentages of the reaction values corresponding to the odors.

In FIG. 14, the characteristics of the coefficient with respect to the humidity are illustrated in a linear manner; however, the present disclosure is not limited thereto. The characteristics of the coefficient with respect to the humidity may be in a non-linear manner.

As illustrated in FIG. 12, a storage 21 stores the reaction values of the sensitive membranes a to j, detected by the substance sensor 10, in correspondence with time of the detection whenever the reaction values are detected. An odor specifier 22 specifies the odor of the gas on the basis of the reaction values of the sensitive membranes a to j, corrected by the coefficient corrector 27. A reaction value calculator 23 calculates the reaction value corresponding to the odor specified by the odor specifier 22 on the basis of the reaction values of the sensitive membranes a to j, corrected by the coefficient corrector 27. A display 25 displays the reaction value corresponding to the odor, calculated by the reaction value calculator 23, so that comparison of the reaction value is enabled in the odor specified by the odor specifier 22.

Processing in the odor detection system 1 according to the present embodiment is now described. Detection processing in the odor detection system 1 is different from the detection processing in the odor detection system 1 according to Embodiment 1 described above.

As illustrated in FIG. 15, the information-processing device 20 waits until a detection instruction is input by operated input (step S1; No). Specifically, a controller 31 waits for the detection instruction by the input operated by an operation device 34, as illustrated in FIG. 7.

When the detection instruction is input by the operated input (step S1; Yes), the information-processing device 20 outputs the detection instruction to the substance sensor 10 (step S2). Specifically, the controller 31 outputs the detection instruction to the substance sensor 10 through the input/output device 36 when the input operated by the operation device 34 is the detection instruction, as illustrated in FIG. 7. The substance sensor 10 detects the substances a to j included in the gas, and outputs a signal indicating the reaction value of each of the sensitive membranes a to j to the input/output device 36. The input/output device 36 converts the signals into the data of the reaction values of the sensitive membranes a to j, and supplies the data to the controller 31.

During this period, the information-processing device 20 waits until a reaction value is received (step S3; No). When the reaction value is received (step S3; Yes), the information-processing device 20 acquires the environmental condition from the environmental sensor 50 (step S21). Specifically, the controller 31 acquires humidity data from the environmental sensor 50 through the input/output device 36, as illustrated in FIG. 7.

Subsequently, the coefficient corrector 27 determines a coefficient on the basis of the acquired environmental information (step S22). For example, the coefficient corrector 27 substitutes the humidity detected by the environmental sensor 50 into a formula for calculation of a coefficient indicated in the graph illustrated in FIG. 14, to determine a coefficient corresponding to the humidity.

Subsequently, the coefficient corrector 27 corrects the reaction values of the sensitive membranes a to j, detected by the substance sensor 10, in correspondence with the sensitive membranes a to j, with coefficients corresponding to the sensitive membranes a to j, set depending on the environmental condition (step S23; coefficient correction step).

Subsequently, the storage 21 stores the reaction values corrected with the coefficients (step S4). Specifically, the controller 31 associates the reaction values, corrected with the coefficients, with detection times, and allows the reaction values to be stored in the external storage 33, as illustrated in FIG. 7.

After step S4, the information-processing device 20 returns to step S1. Whenever steps S1 to S3, S21, S22, S23, and S4 are repeated, a reaction value that is associated with detection time and is corrected is stored in the storage 21, that is, an external storage 33. The detection processing is performed in such a manner.

Like the odor detection system 1 according to Embodiment 1 described above, specification of an odor by the odor specifier 22 (step S13), calculation of a reaction value corresponding to an odor by the reaction value calculator 23 (step S14), calculation of a percentage by a percentage calculator 24 (step S16), display by the display 25 (step S17), and the like are also performed in the odor detection system 1 according to the present embodiment, as illustrated in FIG. 9.

In such analytical display processing, the display 25 can display the reaction values calculated by the reaction value calculator 23 so that comparison of the reaction values is enabled between the specified odors. Moreover, the display 25 displays the percentages of the reaction values corresponding to the odors so that comparison of the percentages is enabled between the specified odors. Further, the display 25 displays the percentages of the reaction values corresponding to the odors and the reaction values corresponding to the odors so that comparison of the percentages and the reaction values is enabled. Further, the display 25 displays at least one of the percentages of the reaction values corresponding to the odors and the reaction values corresponding to the odors so that comparison of the at least one is enabled between the different points of detection.

In the present embodiment, the reaction values of the sensitive membranes are corrected based on humidity. However, the present disclosure is not limited thereto. The environmental condition includes at least one of a humidity, a temperature, and an air pressure. In such a case, coefficients corresponding to the humidity, the temperature, and the air pressure may be included, or a coefficient corresponding to a combination of environmental conditions such as the humidity and the temperature may be included.

In the present embodiment, a coefficient is determined based on the condition of an environment surrounding the sensitive membranes 11, detected by the environmental sensor 50; however, the present disclosure is not limited thereto. For example, a coefficient may be determined based on an environment condition input into the operation device 34 or on an environment condition provided through a communication network.

In accordance with the present embodiment, variations in the accuracy of the detection results of odors can be reduced regardless of changes in the sensitivities of the sensitive membranes a to j, depending on the environmental condition, as described in detail above.

In the odor detection system 1 according to each of the embodiments described above, the reaction values corresponding to odors can be displayed in various manners. As a result, various analyses of odors detected by the odor detection system 1 can be supported. For example, the display of the reaction values corresponding to the odors enables the examination of the sensitivities of the sensitive membranes a to j.

In each of the embodiments described above, the reaction values corresponding to the odors and the percentages of the reaction values are displayed by the bar graphs; however, the present disclosure is not limited thereto. For example, data corresponding to odors may be displayed by another display method such as a circle graph or a polygonal line graph.

When each odor includes one kind of a substance, the reaction value calculator 23 is unnecessary, and the reaction values of the sensitive membranes a to j become the reaction values corresponding to the odors on an as-is basis.

In addition, the hardware or software configuration of the information-processing device 20 of the odor detection system 1 is an example, and can be optionally changed and modified.

A portion that plays a key role in processing in the odor detection system 1 including the controller 31, the memory 32, the external storage 33, the operation device 34, the display device 35, the input/output device 36, the internal bus 30, and the like may be constructed as a dedicated system as described above, or may be implemented using a usual computer system. For example, the odor detection system 1 to execute the processing may be configured by distributing a computer program for executing the operation, stored in a non-transitory computer-readable recording medium (flexible disc, CD-ROM, DVD-ROM, or the like), and by installing the computer program on a computer. A usual computer system may, for example, download the computer program, stored in a storage included in a server device on a communication network such as the Internet, to configure the odor detection system 1.

Only an application program may be stored in a recording medium and a storage, for example, in the case of implementing the function of a computer by sharing between an operating system (OS) and the application program, or in cooperation between the OS and the application program.

A computer program can be superimposed on carrier waves, and distributed through a communication network. For example, the computer program may be posted on a bulletin board system (BBS) on the communication network to distribute the computer program through the network. It is also acceptable to make such a configuration may be made that the processing can be executed by starting the computer program and executing the computer program in a manner similar to that of another application program under the control of the OS.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims priority based on Japanese Patent Application No. 2020-67098, filed on Apr. 2, 2020, the entire disclosure of which is incorporated by reference herein.

INDUSTRIAL APPLICABILITY

The present disclosure can be applied to detection of an odor including a plurality of substances.

REFERENCE SIGNS LIST

1 Odor detection system
10 Substance sensor
11 (a to j) Sensitive membrane
20 Information-processing device
21 Storage
22 Odor specifier
23 Reaction value calculator
24 Percentage calculator
25 Display
27 Coefficient corrector
30 Internal bus
31 Controller
32 Memory
33 External storage
34 Operation device
35 Display device
36 Input/output device
37 Recording medium
39 Program
50 Environmental sensor
a to j Substance

What is claimed is:

1. An odor detection system, comprising:
a substance sensor comprising a sensitive membrane to react with a substance included in an odor of a gas in correspondence with the substance, the substance sensor being configured to detect a reaction value of the sensitive membrane;
an odor specifier to specify the odor of the gas based on the reaction value of the sensitive membrane, detected by the substance sensor;
a reaction value calculator to calculate a reaction value corresponding to the odor specified by the odor specifier based on the reaction value of the sensitive membrane, detected by the substance sensor;
a percentage calculator to calculate a percentage of the reaction value corresponding to the odor specified by the odor specifier to a total of the reaction value corresponding to the odor, calculated by the reaction value calculator; and
a display to display the percentage of the reaction value corresponding to the odor, calculated by the percentage calculator, so that comparison of the percentage is enabled in the odor specified by the odor specifier.

2. The odor detection system according to claim 1, wherein the display displays the reaction value corresponding to the odor, calculated by the reaction value calculator, so that comparison of the reaction value is enabled in the odor specified by the odor specifier.

3. The odor detection system according to claim 1, wherein the display displays the reaction value corresponding to the odor, calculated by the reaction value calculator, and the percentage of the reaction value corresponding to the odor, calculated by the percentage calculator, so that comparison between the reaction value and the percentage is enabled.

4. The odor detection system according to claim 1, further comprising:

a storage to store the reaction value of the sensitive membrane, detected by the substance sensor, in correspondence with time of detection, wherein the display displays at least one of the reaction value corresponding to the odor, calculated by the reaction value calculator, and the percentage of the reaction value corresponding to the odor, calculated by the percentage calculator, so that comparison of the at least one between different detection points is enabled, based on the reaction value of the sensitive membrane, stored in the storage.

5. An odor detection system, comprising:

a substance sensor comprising a sensitive membrane to react with a substance included in an odor of a gas in correspondence with the substance, the substance sensor being configured to detect a reaction value of the sensitive membrane;

a coefficient corrector to correct the reaction value of the sensitive membrane, detected by the substance sensor, in correspondence with the sensitive membrane, with a coefficient corresponding to the sensitive membrane, set depending on a condition of an environment surrounding the sensitive membrane; and an odor specifier to specify the odor of the gas based on the reaction value of the sensitive membrane, corrected by the coefficient corrector.

6. The odor detection system according to claim 5, further comprising:

a reaction value calculator to calculate a reaction value corresponding to the odor specified by the odor specifier based on the reaction value of the sensitive membrane, corrected by the coefficient corrector; and a display to display the reaction value corresponding to the odor, calculated by the reaction value calculator, so that comparison of the reaction value is enabled in the odor specified by the odor specifier.

7. The odor detection system according to claim 6, further comprising:

a percentage calculator to calculate a percentage of the reaction value corresponding to the odor specified by the odor specifier to a total of the reaction value corresponding to the odor, calculated by the reaction value calculator, wherein the display displays the percentage of the reaction value corresponding to the odor, calculated by the percentage calculator, so that comparison of the percentage is enabled in the odor specified by the odor specifier.

8. The odor detection system according to claim 7, wherein the display displays the reaction value corresponding to the odor, calculated by the reaction value calculator, and the percentage of the reaction value corresponding to the odor, calculated by the percentage calculator, so that comparison between the reaction value and the percentage is enabled.

9. The odor detection system according to claim 7, further comprising:

a storage to store the reaction value of the sensitive membrane, detected by the substance sensor, in correspondence with time of detection, wherein the display displays at least one of the reaction value corresponding to the odor, calculated by the reaction value calculator, and the percentage of the reaction value corresponding to the odor, calculated by the percentage calculator, so that comparison of the at least one between different detection points is enabled, based on the reaction value of the sensitive membrane, stored in the storage.

10. The odor detection system according to claim 5, further comprising:

an environmental sensor to detect the condition of the environment, wherein the coefficient corrector corrects the reaction value of the sensitive membrane, detected by the substance sensor, in correspondence with the sensitive membrane, with a coefficient corresponding to the sensitive membrane, set depending on the condition of the environment, detected by the environmental sensor.

11. The odor detection system according to claim 5, wherein the condition of the environment comprises at least one of a humidity, a temperature, and an air pressure.

12. An odor detection method to be executed by an odor detection system to detect an odor of a gas, the odor detection method comprising:

specifying the odor of the gas based on a reaction value of a sensitive membrane, detected by a substance sensor comprising the sensitive membrane to react with a substance included in the odor of the gas in correspondence with the substance;

calculating a reaction value corresponding to the specified odor based on the reaction value of the sensitive membrane, detected by the substance sensor;

calculating a percentage of the reaction value corresponding to the specified odor to a total of the calculated reaction value corresponding to the odor; and displaying the calculated percentage of the reaction value corresponding to the odor so that comparison of the percentage is enabled in the specified odor.

13. An odor detection method to be executed by an odor detection system to detect an odor of a gas, the odor detection method comprising:

correcting a reaction value of a sensitive membrane, detected by a substance sensor comprising the sensitive membrane to react with a substance included in the odor of the gas in correspondence with the substance, in correspondence with the sensitive membrane, with a coefficient corresponding to the sensitive membrane, set depending on a condition of an environment surrounding the sensitive membrane;

specifying the odor of the gas based on the corrected reaction value of the sensitive membrane;

calculating a reaction value corresponding to the specified odor based on the corrected reaction value of the sensitive membrane; and displaying the calculated reaction value corresponding to the odor so that comparison of the reaction value in the specified odors.

14. A non-transitory computer-readable storage medium storing a program causing a computer to function as:

an odor specifier to specify an odor of a gas based on a reaction value of a sensitive membrane, detected by a substance sensor comprising the sensitive membrane to react with a substance included in the odor of the gas in correspondence with the substance;

a reaction value calculator to calculate a reaction value corresponding to the odor specified by the odor specifier based on the reaction value of the sensitive membrane, detected by the substance sensor;

a percentage calculator to calculate a percentage of the reaction value corresponding to the odor specified by the odor specifier to a total of the reaction value corresponding to the odor, calculated by the reaction value calculator; and a display to display the percentage of the reaction value corresponding to the odor, calculated by the percentage calculator, so that comparison of the percentage is enabled in the odor specified by the odor specifier.

15. A non-transitory computer-readable storage medium storing a program causing a computer to function as:

a coefficient corrector to correct a reaction value of a sensitive membrane, detected by a substance sensor comprising the sensitive membrane to react with a substance included in an odor of a gas in correspondence with the substance, in correspondence with the sensitive membrane, with a coefficient corresponding to the sensitive membrane, set depending on a condition of an environment surrounding the sensitive membrane;

an odor specifier to specify the odor of the gas based on the reaction value of the sensitive membrane, corrected by the coefficient corrector;

a reaction value calculator to calculate a reaction value corresponding to the odor specified by the odor specifier based on the reaction value of the sensitive membrane, corrected by the coefficient corrector; and a display to display the reaction value corresponding to the odor, calculated by the reaction value calculator, so that comparison of the reaction value is enabled in the odor specified by the odor specifier.

* * * * *